(12) United States Patent
Mueller

(10) Patent No.: US 6,406,767 B1
(45) Date of Patent: Jun. 18, 2002

(54) MEDICAL SOLUTION TUBING

(75) Inventor: Walter Berndt Mueller, Inman, SC (US)

(73) Assignee: Cryovac, Inc., Duncan, SC (US)

( * ) Notice: Subject to any disclaimer, the term of this patent is extended or adjusted under 35 U.S.C. 154(b) by 0 days.

(21) Appl. No.: 08/396,354

(22) Filed: Feb. 28, 1995

Related U.S. Application Data

(63) Continuation of application No. 07/856,844, filed on Mar. 30, 1992, now abandoned.

(51) Int. Cl.[7] ............................................. F16L 11/04
(52) U.S. Cl. .................. 428/36.91; 428/36.9; 428/515; 428/516; 138/137
(58) Field of Search ..................... 428/36.91, 36.9, 428/515, 516, 520; 138/137

(56) References Cited

U.S. PATENT DOCUMENTS

| | | | |
|---|---|---|---|
| 4,101,699 A | 7/1978 | Stine et al. | 428/36 |
| 4,401,536 A | 8/1983 | Lundell et al. | 204/159 |
| 4,436,778 A | 3/1984 | Dugal | 428/36 |
| 4,551,140 A | 11/1985 | Shinohara | 604/262 |
| 4,565,738 A | 1/1986 | Purdy | 428/349 |
| 4,603,712 A | 8/1986 | Krause | 138/137 |
| 4,627,844 A | 12/1986 | Schmitt | 604/264 |
| 4,643,926 A | 2/1987 | Mueller | 428/35 |
| 4,707,389 A | 11/1987 | Ward | 428/36 |
| 4,772,497 A | 9/1988 | Maasola | 428/35 |
| 4,948,643 A | 8/1990 | Mueller | 428/36 |
| 4,952,451 A | * 8/1990 | Mueller | 428/218 |
| 5,011,720 A | * 4/1991 | Jabarin | 428/36.6 |
| 5,141,809 A | * 8/1992 | Arvedson et al. | 428/349 |

FOREIGN PATENT DOCUMENTS

| | | |
|---|---|---|
| EP | 0216639 | 4/1987 |
| EP | 0232171 | 8/1987 |
| JP | 0082665 | 9/1986 |

* cited by examiner

*Primary Examiner*—Michael A. Williamson
(74) *Attorney, Agent, or Firm*—Thomas C. Lagaly

(57) ABSTRACT

A medical solution tubing useful in combination with medical solution packages and pouches includes an outer layer of polypropylene, ethylene propylene copolymer, or modified ethylene propylene copolymer; an intermediate layer comprising a polymeric elastomer, a blend of a low melt index EVA and a high melt index EVA, EnBA, or blends thereof, or a blend of an EVA-based polymeric adhesive and an elastomeric polyester; and an inner layer comprising EVA, a blend of a low melt index EVA and a high melt index EVA, EMA, EnBA, or blends thereof, or PVC.

5 Claims, 1 Drawing Sheet

MEDICAL SOLUTION TUBING

This application is a continuation of application Ser. No. 07/856,844, filed Mar. 30, 1992, now abandoned.

This invention relates to autoclavable flexible tubing suitable for use with medical solution packaging.

Currently, it is common medical practice to package liquids such as medical solutions for parenteral administration in disposable, flexible pouches. These pouches should be characterized by collapsibility, transparency, and adequate mechanical strength. They must also be able to resist the relatively high temperatures required for heat sterilization of their contents, for example in an autoclave. Typically, medical solutions and the like are autoclaved at about 253° F. for periods of 15 to 30 minutes.

Connector tubing is used in combination with such flexible pouches. This tubing is used to introduce additional materials to the medical solution inside the pouch, and to administer the medical solution to the patient. This connector tubing must be chemically and physically compatible with the medical solution pouch material. The tubing must also be resistant to the heat generated during autoclaving of the medical solution pouch and tubing. When the tubing is used in combination with for example a polycarbonate connector, it sometimes must be sealable to the connector material by means of ultrasonic, radio frequency (RF) or heat sealing. In some cases, a pin heater is inserted into the tubing to heat the inside as well as the outside of the tubing. It is especially required of such tubing that it be flexible without embrittlement or cracking of the tubing. In this regard, it is known that polyvinyl chloride for example becomes brittle at relatively low temperatures.

Of interest is U. S. Pat. No. 4,643,926 issued to Mueller and assigned to a common assignee with the present application. In the '926 patent, a flexible film suitable for medical solution pouches is disclosed. This film may include a sealant layer of ethylene propylene copolymer, modified ethylene propylene copolymer or flexible copolyester; at least one interior layer of a polymeric material which imparts flexibility to the film, such as very low density polyethylene, ethylene propylene monomer blended with ethylene vinyl acetate copolymer, modified ethylene propylene copolymer, ethylene methyl acrylate copolymer, and modified ethylene vinyl acetate copolymer; and an outer layer of copolyester or ethylene propylene copolymer.

Also of interest is U.S. Pat. No. 4,948,643 issued to Mueller and assigned to a common assignee with the present application. The '643 patent discloses a flexible medical solution tubing having an outer layer of e.g. modified EPC, an intermediate layer of e.g. a blend of modified EMA and EVA or VLDPE, and an inner layer of e.g. PVC, or a blend of copolyester and EVA.

OBJECTS

It is an object of the present invention to provide a tubing suitable for use with medical solution packaging, the tubing having good flexibility.

Another object of the present invention is to provide a tubing suitable for use with medical solution packaging characterized by compatibility with prior art packaging and ability to withstand autoclaving of the tubing.

DEFINITIONS

The term "flexible" is used herein to define specific polymeric materials as well as characteristics of a resulting tubing whereby improved flexibility and/or bendability is obtained by the use of these specific polymeric materials. Flexible materials may be characterized by a modulus of preferably less than 50,000 PSI (ASTM D-882-81) and more preferably less than 40,000 PSI (ASTM D-882-81).

The term "polymer", "polymeric", and the like, unless specifically defined or otherwise limited, generally includes homopolymers, copolymers and terpolymers and blends and modifications thereof.

The term "ethylene n-butyl acrylate copolymer" or "EnBA" is used herein to refer to a copolymer formed of ethylene and n-butyl acrylate comonomer wherein the ethylene units are present as more than half of the total copolymer.

The term "intermediate" is used herein to refer to a layer of a multilayer tubing which is bonded on both of its major surfaces to another layer.

The terms "melt flow", "melt index", "MI", and the like are used herein to mean the amount, in grams, of a thermoplastic resin which can be forced through a given orifice under a specified pressure and temperature within 10 minutes. The value should be determined in accordance with ASTM D 1238-79.

The term "ethylene propylene rubber" or EPR is used herein to define a polymeric elastomer obtained by the stereospecific copolymerization of ethylene and propylene, or the two of them with a third monomer such as diene (EPDM). Densities are typically below about 0.88 gm/cc as measured by ASTM D-1505.

The term "ethylene vinyl acetate copolymer" (EVA) is used herein to refer to a copolymer formed from ethylene and vinyl acetate monomers wherein the ethylene derived units in the copolymer are present in major amounts and the vinyl acetate derived units in the copolymer are present in minor amounts.

The term "ethylene propylene copolymer" is used herein to refer to a copolymer formed from polypropylene monomer and minor amounts, usually less than 6%, of ethylene.

The terms "copolyester" and "elastomeric copolyester" (EPET) and the like refer to polyesters synthesized from more than one diol and a dibasic acid. Copolyesters as used herein may also be characterized as copolymers of polyether and polyethylene terephthalate. More preferably copolyesters as used herein may be characterized as polymeric materials derived from 1,4 cyclohexane dimethanol, 1,4 cyclohexane dicarboxylic acid, and polytetramethylene glycol ether, or equivalents of any of the above, as reactants.

The term "modified" and the like is used herein to refer to a polymeric material in which some or all of the substituents are replaced or supplemented by other materials or substituents, providing a change in properties such as improved flexibility or elastomeric properties. For example, a modified ethylene propylene copolymer is for example an ethylene propylene copolymer to which an elastomeric material such as Kraton™ rubber has been added by any means.

The term "polymeric elastomer" is used herein to refer to elastomeric styrene copolymers, EPR, or blends thereof.

SUMMARY OF THE INVENTION

A polymeric tubing comprises an intermediate layer comprising a polymeric elastomer, a blend of a low melt index EVA and a high melt index EVA, EnBA, or blends thereof; an inner layer, bonded to an inner surface of the intermediate layer, comprising a polymeric material selected from EVA, a blend of a low melt index EVA and a high melt index EVA, EMA, EnBA, or blends thereof; and an outer layer, bonded to an outer surface of the intermediate layer, comprising a polymeric material selected from polypropylene, ethylene propylene copolymer, and modified ethylene propylene copolymer.

In another aspect, a polymeric tubing comprises an intermediate layer comprising a blend of an EVA-based polymeric adhesive and an elastomeric copolyester; an inner layer, bonded to an inner surface of the intermediate layer, comprising polyvinyl chloride; and an outer layer, bonded to an outer surface of the intermediate layer, comprising a polymeric material selected from polypropylene, ethylene propylene copolymer, and modified ethylene propylene copolymer.

DETAILED DESCRIPTION OF THE PREFERRED EMBODIMENTS

Figure 1:
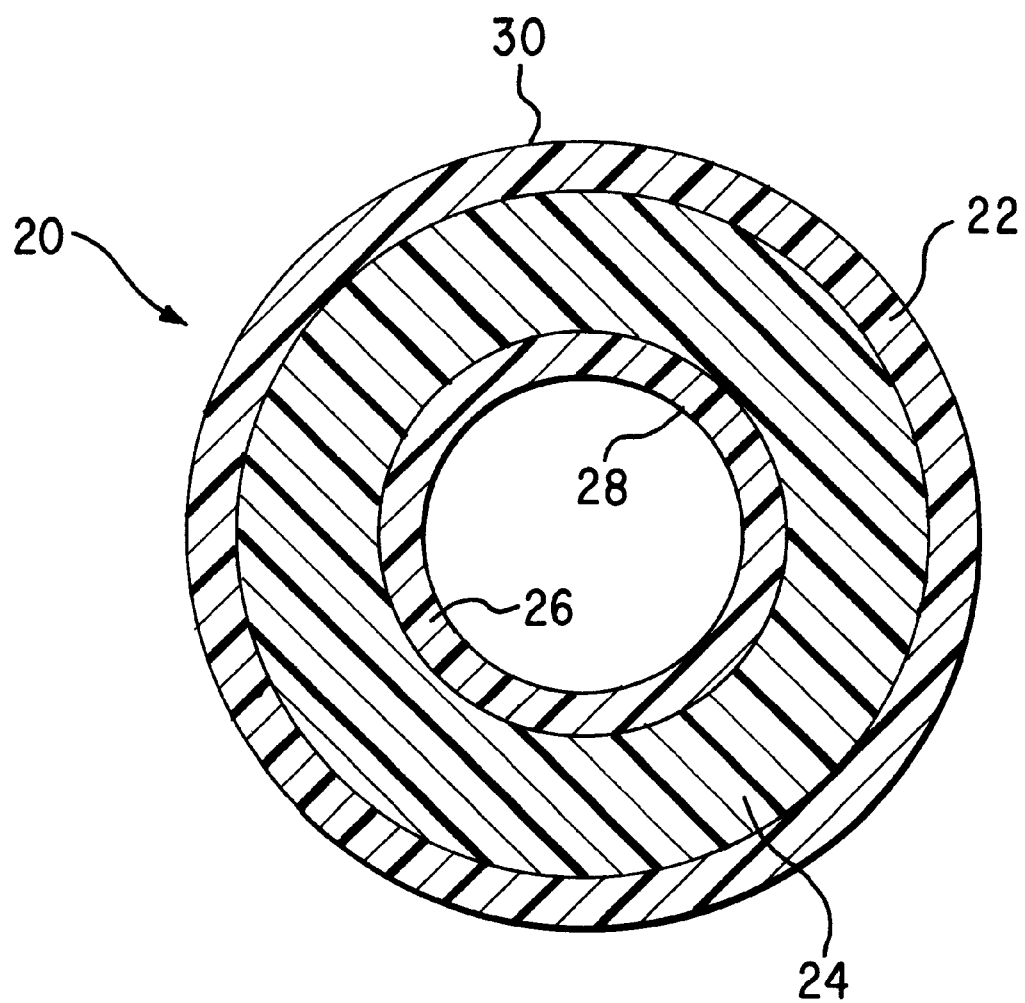
FIG. 1 is a schematic cross-section of a three layer tubing made in accordance with the invention.

FIG. 1 shows a three layer tubing 20 in accordance with the invention. Outer layer 22 is a polypropylene, an ethylene propylene copolymer (EPC), or modified EPC. A suitable EPC is Eltex™ KS 409X6206 available from Solvay. This copolymer has an ethylene content of about 3.8%. A suitable modified EPC is a blend of ethylene propylene copolymer (e.g. Fina Z 9550 available from Fina), and styrene ethylene butylene styrene copolymer (e.g. Kraton 1652 available from Shell). Polyallomers can also be used, such as ethylene propylene block copolymer, available from Eastman as M7853-368A, having a melt flow index of about 12. The inner layer 26 will be in contact at one end with a connector such as a polycarbonate connector. Inner layer 26 will sometimes require sealability with the polycarbonate or other connector material. Sealing may be done by e.g. ultrasonic sealing, heat sealing, or RF sealing depending on the materials used.

Intermediate layer 24 can be any of various polymeric elastomers which impart flexibility to the resulting film. Especially preferred materials are elastomeric styrene copolymers such as those available from Shell as Kraton™ resins. These include styrene ethylene butylene styrene copolymer (SEBS) (e.g. G 2706, G 2703, and G 2712); styrene isoprene styrene copolymer (SIS) (e.g. D 1107); and styrene butadiene styrene copolymer (SBS) (e.g. D 1102). Also useful in intermediate layer 24 is EPR, such as Tafmer™ resins from Mitsui, e.g. Tafmer P-0480 and P-0680.

Another material suitable for layer 24 is a blend of a low melt index (LMI) EVA (i.e. MI is less than 1) and a high melt index (HMI) EVA (i.e. MI is greater than or equal to 1). An example of an LMI EVA is Elvax™ 3165 available from Du Pont, and having a vinyl acetate content of about 18% by weight and a melt index of about 0.7. An example of an HMI EVA is Elvax 3182, also available from Du Pont, and having a vinyl acetate content of about 28% by weight and a melt index of about 3. These respective LMI and HMI EVA copolymers can be blended in any suitable percentages from 1 to 99% of each material.

Intermediate layer 24 can also be an EnBA such as EA719.009 from Quantum/USI.

Layer 24 can also comprise a blend of any of the materials indicated above for layer 24.

Inner layer 26 of the three layer embodiment of the present invention is preferably an ethylene vinyl acetate copolymer, such as those mentioned above for intermediate layer 24.

The EVA of inner layer 26 can be irradiated to improve certain properties of the tubing, but irradiation can also adversely affect the tubing in some respects.

An alternative for layer 26 is a blend of an LMI EVA and an HMI EVA, such as the blend given above for intermediate layer 24.

An alternative for layer 26 is the use of ethylene methyl acrylate copolymer (EMA) such as Chevron DS 1193 having 33% methyl acrylate and a melt index of about 2.

Another alternative is the blending of either LMI or HMI EVA, or both, with EMA. The respective percentages of EVA and EMA can range from 1 to 99% of each material. This alternative is especially useful in applications where tubing is solvent welded to PVC fittings, using a solvent such as cyclohexanone.

Still another alternative for inner layer 26 is an EnBA such as EA719.009 from Quantum/USI.

Layer 26 can also comprise a blend of any of the materials indicated above for layer 26.

The materials of inner layer 26 are especially chosen for their heat resistance so that the tubing may be autoclaved along with the accompanying medical solution pouch and still maintain its structural integrity.

An alternative tubing structure includes the same outer layer as described above for tubing outer layer 22; an intermediate layer 24 comprising a blend of an EVA-based polymeric adhesive and an elastomeric copolyester; and an inner layer comprising polyvinyl chloride (PVC). An example of the EVA-based polymeric adhesive is Bynel™ E 361 available from Du Pont. An example of the elastomeric copolyester is ECDEL 9965 available from Eastman Chemical.

The tubing after coextrusion or other suitable processing by conventional means may optionally be cross-linked by radiation techniques well known in the art. This irradiation may strengthen the tubing particularly for autoclaving purposes. Alternatively, a chemical cross-linking agent may be introduced to the resin melt of any or all of the layers discussed above prior to extrusion to effect the cross-linking of one or more layers of the tubing.

EXAMPLES

Exemplary multi-layer structures were coextruded by conventional means, and in one case (Example 6) irradiated. These structures are viewed as potential replacements for polyvinyl chloride tubing. Examples 1 through 11 are listed below with their respective formulations, beginning with the outer layer and ending with the inner layer. All examples except Example 10 were actually produced. Examples 1 through 11 include the following materials:

| MATERIAL | TRADE DESIGNATION |
|---|---|
| EPC#1 | Z 9550 |
| SEBS#1 | KRATON G 2706X |
| SEBS#2 | KRATON G 2703 |
| SEBS#3 | KRATON G 1652 |
| Modified EPC: | 70% Z9550 + 30% KRATON G 1652 |
| SIS: | KRATON D 1107 |
| EVA#1: | ELVAX 3165 |
| EVA#2: | ELVAX 3182 |
| EMA: | CHEVRON DS 1193 |
| EPR: | TAFMER P 0480 |
| ADHESIVE: | BYNEL E 361 |

| MATERIAL | TRADE DESIGNATION |
|---|---|
| EPET: | ECDEL 9965 |
| EnBA: | EA719.009 |
| PVC: | TEKNOR APEX 3300R-68NT |

In Example 1 the multilayer tubing comprised modified EPC/SEBS#1/EVA#1.

In Example 2 the multilayer tubing comprised modified EPC/SEBS#2/EVA#1.

In Example 3 the multilayer tubing comprised modified EPC/SIS/EVA#1.

In Example 4 the multilayer tubing comprised modified EPC/EPR/EVA#1.

In Example 5, the multi-layer tubing comprised modified EPC/SEBS#1/80% EVA#1+20% EVA#2.

In Example 6, the multi-layer tubing comprised modified EPC/SEBS#1/EVA#1 (irradiated).

In Example 7, the multi-layer tubing comprised modified EPC/SEBS#2/60% EVA#1+40% EMA.

In Example 8, the multi-layer tubing comprises modified EPC/SEBS/50% EVA#2+50% EMA.

In Example 9, the multi-layer tubing comprised modified EPC/50% EnBA+50% EPR/EnBA.

In Example 10, the multi-layer tubing comprised modified EPC/50% EVA#1+50% EVA#2/EnBA.

In Example 11, the multi-layer tubing comprised modified EPC/50% ADHESIVE+50% EPET/PVC.

It should be noted that the detailed description and specific examples which indicate the presently preferred embodiments of the invention are given by way of illustration only. Various changes and modifications within the spirit and scope of the claims will become apparent to those of ordinary skill in the art upon review of the above detailed description and examples.

What is claimed is:

1. A polymeric medical tubing comprising:
   a) an intermediate layer comprising a polymeric material selected from the group consisting of
      i) ethylene n-butyl acrylate copolymer,
      ii) blends of ethylene n-butyl acrylate copolymer with a polymeric elastomer,
      iii) a blend of a low melt index EVA and a high melt index EVA, and
      iv) a blend of a low melt index EVA, a high melt index EVA, and an elastomer;
   b) an inner layer, bonded to an inner surface of the intermediate layer, and comprising a polymeric material selected from the group consisting of
      i) a blend of a low melt index EVA and a high melt index EVA,
      ii) ethylene methyl acrylate copolymer,
      iii) ethylene n-butyl acrylate copolymer, and
      iv) blends thereof; and
   c) an outer layer, bonded to an outer surface of the intermediate layer, and comprising a polymeric material selected from the group consisting of
      i) polypropylene,
      ii) ethylene propylene copolymer, and
      iii) modified ethylene propylene copolylmer.

2. The tubing of claim 1 wherein the intermediate layer comprises an elastomer selected from the group consisting of:
   a) styrene ethylene butylene styrene copolymer;
   b) styrene isoprene styrene copolymer;
   c) styrene butadiene styrene copolymer;
   d) ethylene propylene rubber; and
   e) blends of the above.

3. The tubing of claim 1 wherein the inner layer comprises a blend of 1 to 99% by weight of a low melt index EVA, and 99% to 1% of a high melt index EVA.

4. The tubing of claim 1, wherein the inner layer comprises a blend of (i) ethylene vinyl acetate copolymer in an amount of from 1 to 99 weight percent and (ii) ethylene methyl acrylate copolymer in an amount of from 99 to 1 weight percent, to facilitate solvent welding of said tubing to pvc-type fittings.

5. The tubing of claim 1, wherein the inner layer comprises a blend of (ii) a blend of a low melt index EVA and a high melt index EVA in an amount of from 1 to 99 weight percent and (iii) ethylene methyl acrylate copolymer in an amount of from 99 to 1 weight percent, to facilitate solvent welding of said tubing to pvc-type fittings.

* * * * *